United States Patent
Berger et al.

(10) Patent No.: US 7,985,259 B2
(45) Date of Patent: Jul. 26, 2011

(54) ACETABULAR CUP CONVERSION RING

(75) Inventors: Richard A. Berger, Chicago, IL (US); Erin M. Johnson, Columbia City, IN (US); Archie W. Newsome, Mentone, IN (US); Randy L. Schlemmer, Bremen, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 67 days.

(21) Appl. No.: 12/504,155

(22) Filed: Jul. 16, 2009

(65) Prior Publication Data
US 2009/0287312 A1    Nov. 19, 2009

Related U.S. Application Data

(62) Division of application No. 11/401,727, filed on Apr. 11, 2006, now abandoned.

(51) Int. Cl.
*A61F 2/32*    (2006.01)
(52) U.S. Cl. .................. 623/22.29; 623/22.2; 623/22.26
(58) Field of Classification Search ............... 623/22.25, 623/22.26, 22.28, 22.29, 22.19, 22.2
See application file for complete search history.

(56) References Cited

U.S. PATENT DOCUMENTS

| | | |
|---|---|---|
| 2,339,771 A | 1/1944 | Davies |
| 3,179,448 A | 4/1965 | Jones |
| 3,683,421 A | 8/1972 | Martinie |
| 3,903,549 A | 9/1975 | Deyerle |
| 3,978,528 A | 9/1976 | Crep |
| 4,058,024 A | 11/1977 | Gordon |
| 4,355,825 A | 10/1982 | Leicht |
| 4,642,123 A | 2/1987 | Noiles |
| 4,678,472 A | 7/1987 | Noiles |
| 4,770,658 A | 9/1988 | Geremakis |
| 4,886,113 A | 12/1989 | Ross et al. |
| 5,092,897 A | 3/1992 | Forte |
| 5,104,399 A | 4/1992 | Lazarus |
| 5,282,864 A | 2/1994 | Noiles et al. |
| 5,310,408 A | 5/1994 | Schryver et al. |
| 5,314,491 A | 5/1994 | Thongpreda et al. |
| 5,362,311 A | 11/1994 | Amino et al. |
| 5,383,938 A | 1/1995 | Rohr et al. |
| 5,392,596 A | 2/1995 | Nolsapple et al. |
| 5,507,824 A | 4/1996 | Lennox |

(Continued)

FOREIGN PATENT DOCUMENTS
EP    0086879 A1    8/1983
(Continued)

OTHER PUBLICATIONS

Webpage—Zimmer Product—Epsilon Durasul Constrained Insert, 3 pages, 2007 Zimmer, Inc. (EpsilonDurasul).

(Continued)

*Primary Examiner* — Bruce E Snow
(74) *Attorney, Agent, or Firm* — Baker & Daniels LLP

(57) ABSTRACT

An acetabular implant for hip replacement surgery includes a shell component and first and second alternative bearing components interchangeably engageable with the shell component to provide a choice in bearing materials. The shell component has an engagement mechanism suitable for locking engagement with the first alternative shell component. A conversion ring is lockingly engageable with the shell component to adapt the shell component to provide an engagement mechanism suitable for locking engagement with the second alternative shell component.

17 Claims, 3 Drawing Sheets

U.S. PATENT DOCUMENTS

| | | |
|---|---|---|
| 5,549,691 A | 8/1996 | Harwin |
| 5,549,701 A | 8/1996 | Mikhail |
| 5,593,445 A | 1/1997 | Waits |
| 5,725,591 A | 3/1998 | DeCarlo et al. |
| 5,824,108 A | 10/1998 | Huebner |
| 5,989,294 A | 11/1999 | Marlow |
| 6,217,832 B1 | 4/2001 | Betta et al. |
| 6,231,612 B1 | 5/2001 | Balay et al. |
| 6,328,764 B1 | 12/2001 | Mady |
| 6,368,354 B2 * | 4/2002 | Burstein et al. ............ 623/22.28 |
| 6,475,243 B1 | 11/2002 | Sheldon |
| 6,527,808 B1 | 3/2003 | Albertorio et al. |
| 6,589,284 B1 | 7/2003 | Silberer |
| 6,610,097 B2 | 8/2003 | Serbousek et al. |
| 6,827,742 B2 | 12/2004 | Hayes et al. |
| 6,916,342 B2 | 7/2005 | Frederick |
| 7,040,407 B2 | 5/2006 | Jennings et al. |
| 7,115,145 B2 | 10/2006 | Richards |
| 2001/0037156 A1 | 11/2001 | Burstein et al. |
| 2002/0068980 A1 | 6/2002 | Serbousek et al. |
| 2003/0050703 A1 | 3/2003 | Harris et al. |
| 2003/0105529 A1 | 6/2003 | Synder et al. |
| 2003/0187512 A1 | 10/2003 | Frederick et al. |
| 2005/0004677 A1 | 1/2005 | Johnson |
| 2005/0004678 A1 | 1/2005 | Richards |
| 2005/0102034 A1 | 5/2005 | Hayes et al. |
| 2005/0240276 A1 | 10/2005 | Shea et al. |
| 2006/0149256 A1 | 7/2006 | Wagner et al. |
| 2006/0226470 A1 | 10/2006 | Case |
| 2006/0241781 A1 | 10/2006 | Brown et al. |
| 2007/0106390 A1 | 5/2007 | Richards |
| 2007/0239283 A1 | 10/2007 | Berger |

FOREIGN PATENT DOCUMENTS

| | | |
|---|---|---|
| EP | 0694294 A1 | 1/1996 |
| EP | 0773007 A1 | 5/1997 |
| FR | 2357235 A1 | 2/1978 |
| FR | 2684544 A1 | 6/1993 |
| FR | 2805151 A1 | 8/2001 |
| FR | 2824258 A1 | 11/2002 |
| GB | 2306330 A | 5/1999 |
| WO | WO00/64383 A1 | 11/2000 |

OTHER PUBLICATIONS

Office Action mailed Jun. 18, 2007, in U.S. Appl. No. 11/104,351.

Wright Medical Technology, Inc. "Lineage Acetabular Cup System Surgical Technique," copyright 2003, Arlington, TN 38002 (12 pages) (LineageCeramicST).

ISR and WO issued in related International App. No. PCT/US2007/066309 on Aug. 23, 2007.

* cited by examiner

ACETABULAR CUP CONVERSION RING

CROSS-REFERENCE TO RELATED APPLICATIONS

This application is a division of U.S. patent application Ser. No. 11/401,727, filed on Apr. 11, 2006, entitled "Acetabular Cup Conversion Ring", the entire disclosure of which is expressly incorporated by reference herein.

FIELD OF THE INVENTION

The present invention relates to acetabular implants for hip replacement surgery. In particular, the present invention relates to acetabular implants including a shell component and alternative bearing components interchangeably engageable with the shell component to provide a choice of bearing materials.

BACKGROUND

Total hip replacement surgery is commonly performed to alleviate pain and loss of function in injured or diseased hip joints. During this surgery, the articulating surfaces of the hip joint are replaced with prosthetic bearing components. The replacement components generally include a femoral component having a convex bearing surface and an acetabular cup component having a mating concave bearing surface.

Modular prosthetic components have become popular because they allow the surgeon to assemble components in a variety of configurations at the time of surgery to meet specific patient needs and surgeon preferences. For example, modular acetabular components generally include separate shell and liner components that can be assembled in a variety of configurations of shell surface finish, shell outer diameter, liner inner diameter, and liner bearing material. With a modular acetabular component, it is desirable to lock the shell and liner together to prevent expulsion of the liner and to minimize debris producing wear between them. Typically, the engagement mechanism is formed adjacent the equator of a hemispherical shell and liner to maximize the engagement area and the resulting holding power of the engagement mechanism.

Various liner bearing materials are in use. The liners vary in hardness, friction coefficient with different paired ball heads, weight, and wear resistance. Polymers, including ultrahigh molecular weight polyethylene (UHMWPE), are commonly used as bearing materials paired with an opposing metal, ceramic, or other composition ball head. The wear resistance of UHMWPE has been improved by irradiating it to cause changes in its chemical and mechanical properties. As the wear properties are improved the bulk physical properties change also. Other materials, including metals and ceramics, have also been used for acetabular bearings. These materials vary from one another in terms of their hardness, resilience, brittleness, and other physical properties. Because of this variation, various mechanisms have been developed for engaging acetabular liners with their mating shells. Different engagement mechanisms are suitable for different liner and shell material combinations. These engagement mechanisms include snap-fit, cylindrical press-fit, taper-fit, threaded engagement, and other suitable locking mechanisms. It is desirable to be able to alternately fit different liners into a common shell to reduce inventory while allowing surgeon choice in liner selection. It is also desirable to allow intraoperatively changing from one liner to another without having to remove a shell that has already been placed in the surgical site during a primary surgery or one that has become well fixed and only needs liner replacement in a revision surgery.

U.S. Pat. No. 6,475,243 issued to Sheldon et al. Nov. 5, 2002. The '243 patent teaches a shell and liner arrangement that permits alternative engagement of liners made of different materials and having different engagement mechanisms. The '243 shell includes both a snap-fit engagement mechanism and a taper-fit engagement mechanism formed in the interior of the shell adjacent the shell equator. The snap-fit mechanism includes a pair of annular grooves formed in the shell for receiving a pair of annular projections protruding from the liner. One of the annular projections deforms upon insertion of the liner into the shell and snaps back into engagement with one of the annular grooves to retain the liner in the shell. The other annular projection seats in the other annular groove and engages a projection formed in the groove to prevent rotation of the liner relative to the shell. The snap-fit mechanism is suitable for relatively soft liner materials that can deform to snap into the annular ring and that can deform to engage the antirotation feature.

The taper-fit engagement mechanism includes a tapered seat formed on the inside of the shell adjacent the equator for receiving a liner having a tapered exterior surface. The taper-fit engagement mechanism is suitable for relatively hard liner materials. The annular grooves of the snap-fit engagement mechanism are superimposed with the taper-fit engagement mechanism such that the annular grooves interrupt the tapered seat and consequently reduce the bearing area of the tapered seat and potentially create stress risers at the taper surface.

U.S. Pat. No. 6,610,097 issued to Serbousek et al. Aug. 26, 2003. The '097 patent teaches a conventional hip cup arrangement including a metal shell and a polyethylene bearing insertable into the shell. The polyethylene bearing is part of a subassembly including a metal liner permanently attached during manufacture to the polyethylene bearing. The liner provides a metal taper surface to facilitate taper seating of the subassembly into the shell.

SUMMARY

The present invention provides an acetabular implant for hip replacement surgery including a shell component and first and second alternative bearing components interchangeably engageable with the shell component to provide a choice in bearing components. The shell component has a first engagement mechanism suitable for engaging the first alternative shell component. A conversion ring is engageable with the shell component to adapt the shell component to provide a second engagement mechanism suitable for engagement with the second alternative shell component.

In one aspect of the invention, the conversion ring includes a ring shaped body having a sidewall defining an outer surface and an inner surface and extending axially from a first end to a second end. A first engagement mechanism is formed on the outer surface and is engageable with the first engagement mechanism of the acetabular shell component in axial locking arrangement. A second engagement mechanism is formed on the inner surface and is engageable with the second engagement mechanism of the second alternative bearing component in axial locking arrangement.

In another aspect of the invention, a kit includes a shell component, first and second bearing components, and a conversion ring having a sidewall defining an outer surface and an inner surface and extending axially from a first end to a second end. The outer surface defines a complimentary first engagement mechanism engageable with the first engagement mechanism of the shell component. The inner surface defines a second engagement mechanism engageable with the second bearing component.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Figure 1:
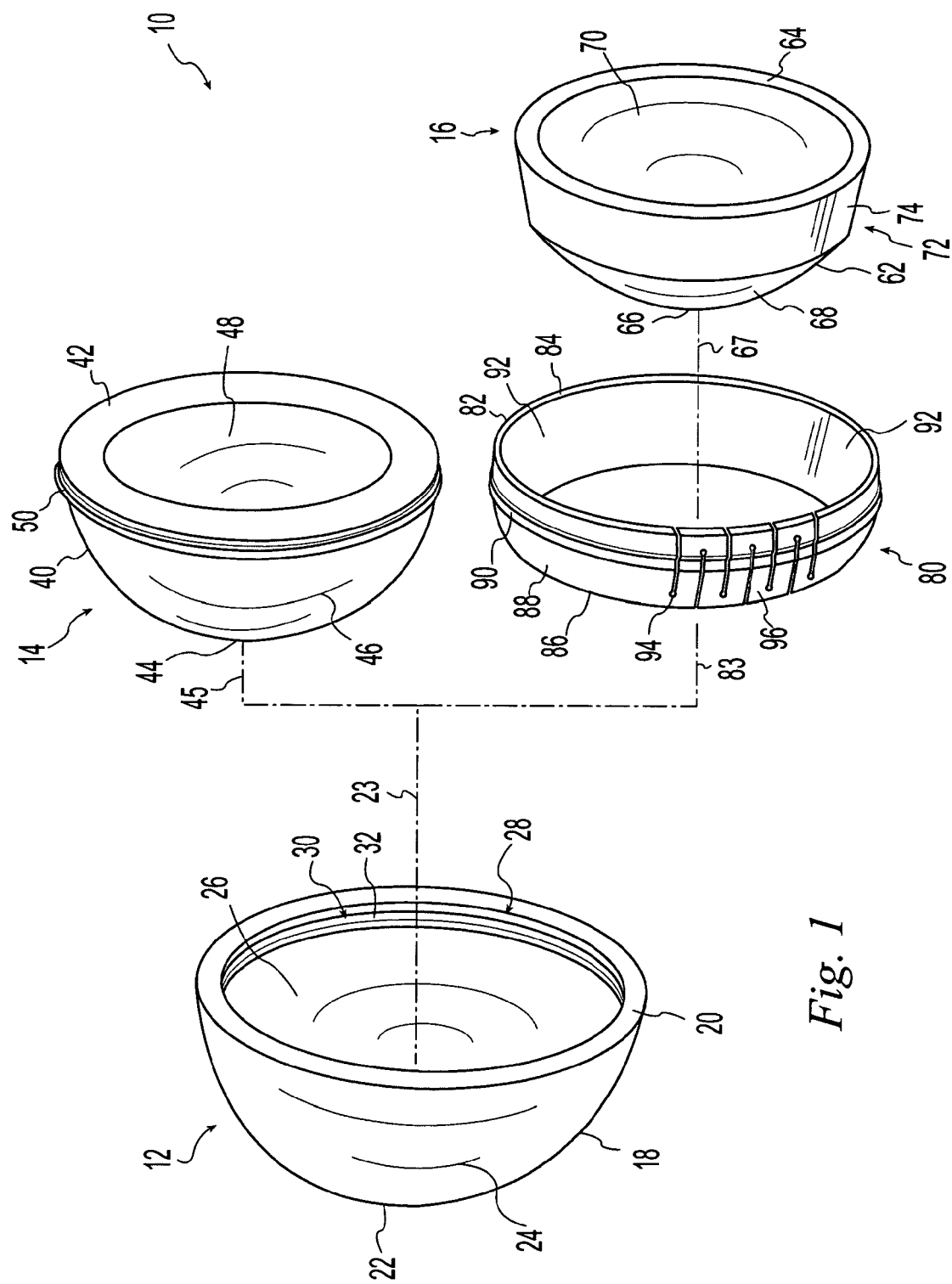
FIG. 1 is a perspective view of an illustrative exemplary kit of acetabular components for assembling alternative acetabular hip implants.

Embodiments of the present invention include an acetabular cup conversion ring engageable with an acetabular shell component. The shell component includes a first engagement mechanism for engaging a first alternative bearing component to couple it to the shell component. The conversion ring is engageable with the first engagement mechanism to convert the shell component from the first engagement mechanism to a second engagement mechanism suitable for coupling a second alternative bearing component to the shell. Thus, the conversion ring converts the shell first engagement mechanism to provide a second alternative engagement mechanism for an alternative bearing component to facilitate a choice in bearing components. For example, alternative bearing components may be provided that differ in material, size, shape, and/or other parameter. For example, the alternative bearing components may be provided in a variety of materials such as polyethylene, crosslinked polyethylene, metal, ceramic, and/or other suitable materials.

The conversion ring may be closed at one end or it may be open at both ends to permit the bearing component to extend through the ring. This allows the bearing component to occupy the full depth of the shell component and thereby maximize the bearing thickness at the polar region. The conversion ring may be generally in the form of a hollow ring or band. The conversion ring may include a first engagement mechanism formed on its outer surface that is engageable with the first engagement mechanism formed on the inside of the shell. The conversion ring may include a second engagement mechanism formed on its inner surface that is engageable with the second engagement mechanism of an alternative bearing component. The first and second engagement mechanisms may be of the same or a different type. Engagement mechanism types may include snap-fit, press-fit, taper-fit, threaded, and/or other suitable engagement mechanism types. The second engagement mechanism may be configured for a particular type of bearing component. Multiple conversion rings may be provided in a variety of configurations to adapt a variety of different bearing components to a common shell. For example, the first engagement mechanism may provide a snap-fit to engage a relatively resilient bearing component directly in the shell. A relatively rigid alternative bearing component may be more suited to a taper-fit engagement mechanism. In this example, the conversion ring would include a complimentary snap-fit engagement mechanism on its outer surface engageable with the shell and a complimentary taper-fit engagement mechanism on its inner surface engageable with the alternative bearing component. In another example, the first engagement mechanism may include a taper-fit suited to the first bearing component and the second bearing component may require a taper-fit having a different taper angle. In this example, the conversion ring would have a taper-fit on both its inner and outer surfaces but the angle of each taper-fit would be different.

The conversion ring may be made of a variety of materials including polymers, metals, ceramics, and combinations thereof. Where a snap-fit engagement mechanism is employed for one of the first and second engagement mechanisms, a degree of resiliency is required to allow the snap-fit to function. The conversion ring, or at least the snap-fit portion of the conversion ring, may be made of a relatively resilient material to facilitate the snap fit. Alternatively, the conversion ring may be made of a relatively rigid material that is shaped to impart resiliency to selected portions of the ring. For example, the conversion ring may be made of a relatively rigid metal with a portion of the ring being removed to allow the ring to compress and expand to function in a snap-fit engagement mechanism. For example the conversion ring may be cut through its sidewall to allow the ring to compress to a smaller diameter. In another example, the ring sidewall may remain a continuous band but may include multiple cuts extending part-way through the sidewall and originating on alternating opposite sides to form the sidewall into a serpentine sidewall that is more resilient than the uncut sidewall.

Figure 2:
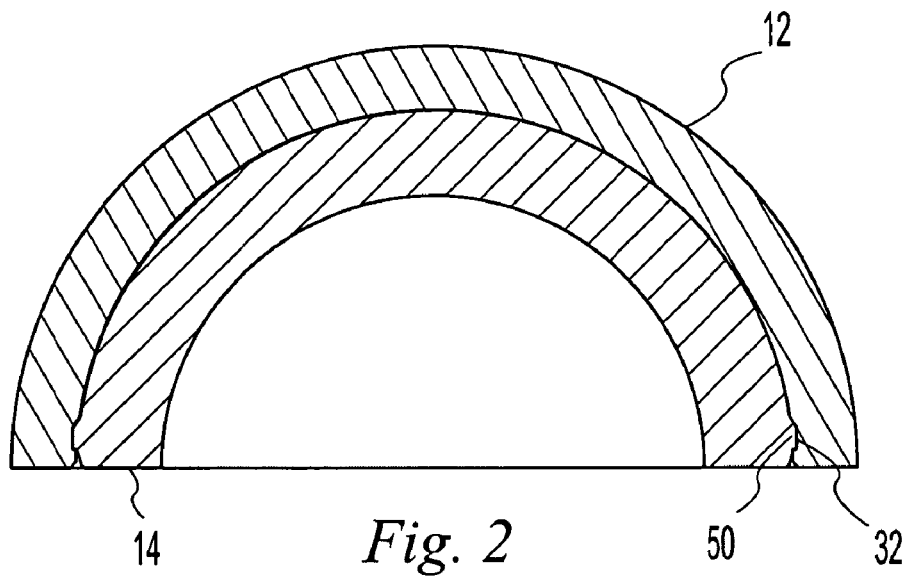
FIG. 2 is a cross sectional view of one illustrative alternative acetabular hip component assembled from the kit of FIG. 1.
Figure 3:
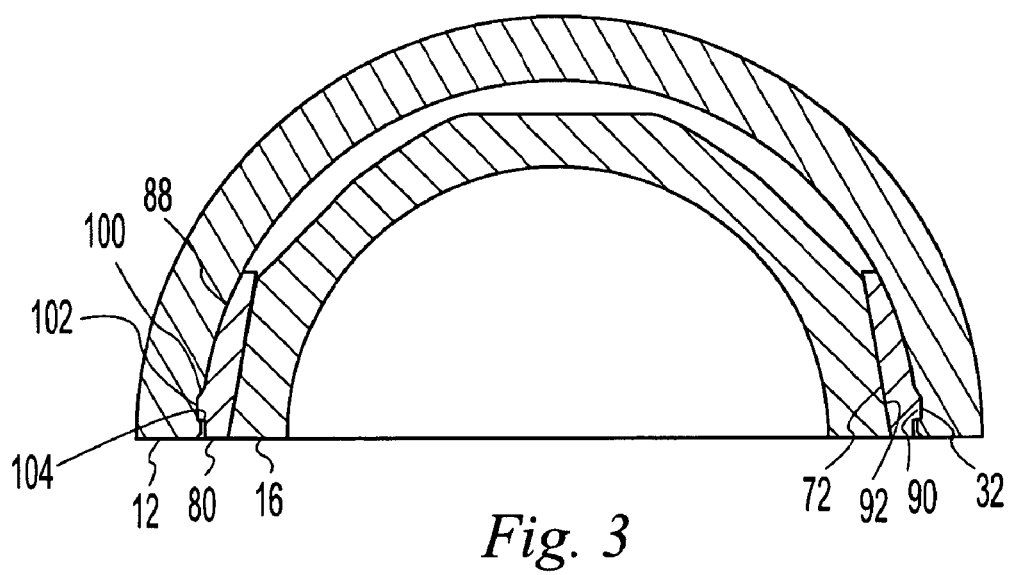
FIG. 3 is a cross sectional view of another illustrative alternative acetabular hip component assembled from the kit of FIG. 1.

FIGS. 1-3 depict an illustrative example of an acetabular cup assembly 10 including a shell component 12 and alternative first and second bearing components 14, 16. The shell component 12 includes a hollow hemispherical body 18 extending from an equatorial rim 20 to a polar end 22 along an axis 23 and defining a convex exterior surface 24 and a concave interior surface 26. The rim 20 defines a circular opening 28 communicating with the interior surface 26. A first engagement mechanism 30 in the form of a snap-fit engagement mechanism is formed on the interior surface 26 adjacent the rim 20. The engagement mechanism includes an annular groove 32 formed into the body 18.

The first bearing component 14 includes a hollow hemispherical body 40 extending from an equatorial rim 42 to a polar end 44 along an axis 45 and defining a convex exterior surface 46 and a concave interior surface 48. The first bearing component includes a complimentary snap-fit engagement mechanism including an annular projection 50 sized to fit within the annular groove 32. When the first bearing component 14 is pressed into the shell component 12, the annular projection 50 deforms resiliently to fit through the opening 28 and snaps into the groove 32 to retain the first bearing component 14 in the shell component 12. In the illustrative example, the first bearing component 14 is made of polyethylene.

The second bearing component 16 includes a hollow hemispherical body 62 extending from an equatorial rim 64 to a polar end 66 along an axis 67 and defining a convex exterior surface 68 and a concave interior surface 70. The illustrative second bearing component 16 is made of a relatively rigid material such as metal or ceramic and includes a tapered exterior surface 72 adjacent the rim 64.

A conversion ring 80 includes a hollow body 82 having an axis 83 extending from a first end 84 to a second end 86 along the axis 83. The conversion ring 80 includes an outer surface 88 adapted to engage the shell component 12. The outer surface 88 includes an annular projection 90 engageable with the annular groove 32 of the shell component 12. The conversion ring includes a tapered inner surface 92 engageable with the tapered exterior surface 72 of the second bearing component 16. In the illustrative example, the conversion ring 80 and second bearing component 16 engage one another in a self-locking taper engagement. The illustrative conversion ring 80 is made of a relatively rigid material, such as metal, to provide rigid support to the relatively rigid second bearing component 16 and to facilitate a tight self-locking taper-fit. The conversion ring 80 is intraoperatively engageable and disengageable with the shell component 12 and the second bearing component 16. Thus, intraoperative selection of a conversion ring 80, a bearing component 16, and a shell component 12 is possible as well as intraoperative changing of the components using manual manipulation and readily available tools. Similarly, during a revision surgical procedure, the bearing 16, ring 80, and shell 12 may be readily separated to facilitate replacement of the bearing 16 and/or the ring 80.

The illustrative conversion ring 80 is provided with a plurality of slits 94 cut part-way through the body 82 and originating alternately from the first and second ends 84, 86 to form a portion of the sidewall into a serpentine sidewall 96. In the illustrative conversion ring 80, the serpentine sidewall 96 is shown over a small portion of the body 82. The serpentine pattern may also be formed in multiple discrete locations around the body 82 or it may be formed entirely around the body 82. When the conversion ring 80 is pressed into the shell component 12, the slits 94 allow the conversion ring 80 to compress to a smaller diameter to permit the annular projection 90 to fit through the opening 28 and snap into the groove 32 to retain the second bearing component 16 in the shell component 12. A single slit 94 cut all the way through the conversion ring 80 may be provided to permit the conversion ring 80 to compress. However, the multiple alternating slits 94 are advantageous since each slit 94 can be much narrower than would be required by a single slit 94 to provide the same degree of compressibility. By providing multiple narrow slits 94, the localized interruption of the inner tapered surface 92 by each slit is minimized. The alternating pattern of slits also provides for continuous, albeit serpentine, support of the second bearing component around the entire circumference of the conversion ring 80.

Once the conversion ring 80 is snapped into the shell component 12, the conversion ring 80 resiliently expands to abut the outer surface 88 of the conversion ring 80 against the interior surface 26 of the shell component 12. This abutment prevents the conversion ring 80 from expanding to a larger diameter when the second bearing component 16 is inserted into the shell and ring assembly. Likewise, the taper-fit engagement of the second bearing component 16 with the conversion ring 80 prevents the conversion ring from collapsing and exiting the shell 12 once the second bearing component 16 is engaged with the conversion ring 80.

FIGS. 2-3 provide more detailed views of the illustrative engagement mechanism. The first bearing component 14 snap-fit engagement with the shell component 12 is shown in FIG. 2. The conversion ring 80, second bearing component 16, and shell component 12 engagements are shown in FIG. 3. The taper engagement between the second bearing component 16 and the conversion ring 80 includes continuous taper surfaces 72, 92 providing support for the bearing component at its equator. The illustrative annular projection 90 of the conversion ring 80 includes a ramped leading edge 100 angling outwardly from the outer surface 88 to ease insertion of the conversion ring 80 into the shell component 12. A seating portion 102 extends from the leading edge 100 generally parallel to the outer surface 88. A shoulder 104 extends radially inwardly from the seating portion 102. The annular groove 32 in the shell component has a shape complimentary to the annular projection 90. As the conversion ring 80 is inserted into the shell component 12, the ramped leading edge 100 engages the opening 28 such that continued axial pressure causes the conversion ring 80 to compress and the annular projection 90 to slide along the inner surface of the shell component 12 until it snaps into the annular groove 92. With just the conversion ring 80 in the shell component 12, the conversion ring 80 can be readily pried out of the shell component 12. When the bearing component 16 is seated in the conversion ring 80 it presses the conversion ring 80 into engagement with the shell component 12 to prevent it from collapsing and being disengaged with the shell component. Removal of the bearing component 16 again frees the conversion ring 80 to be compressed and removed. Preferably, the seating portion 102 bottoms in the annular groove 32 to form a press fit upon insertion of the bearing component 16 to prevent positioning of the conversion ring 80 in the shell component 12.

Figure 4:
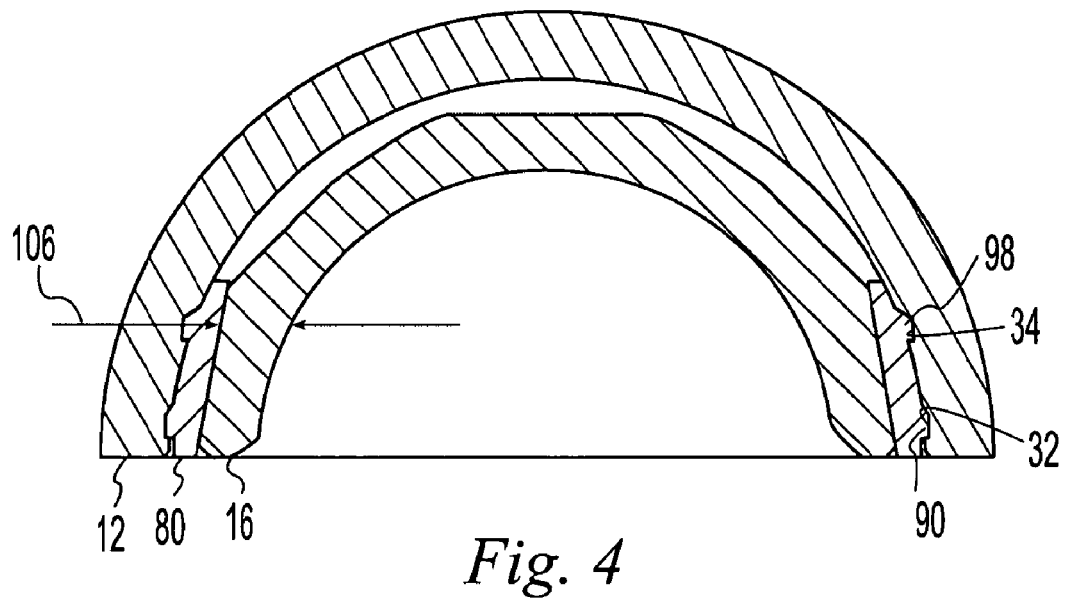
FIG. 4 is an alternative arrangement for the snap-lock mechanism of the acetabular hip component of FIG. 3.

FIG. 4 illustrates an alternative configuration of the engagement mechanism comprising a second annular groove 34 spaced axially into the cup from the first annular groove 32. The conversion ring 80 may include a second annular projection 98 engageable with the second annular groove 32 to provide more support for the conversion ring 80 and second bearing component 16 (as shown). Alternatively, one of the annular grooves 32, 34 may be engaged by the first bearing component 14 and the other annular groove may be engaged by the conversion ring 80 (not shown). For example, the first bearing component 14 may engage the annular groove 32 nearer the equator of the shell component 12 and the conversion ring 80 may engage the annular groove 34 further from the equator of the shell component 12. This arrangement may be advantageous where, for example, the first annular groove 32 is positioned to mate with existing bearing components with an annular projection near the equator and where the second annular groove 34 and conversion ring annular projection 98 are positioned axially inwardly from the equator to position them near a thicker portion 106 of the bearing component 16 to support the bearing component 16 at the thicker portion 106.

In use, a decision is made as to which of the alternative bearing components 14, 16 is desired. If the first bearing component 14 is to be used, it is snapped directly into the shell component 12. If the second bearing component 16 is to be used, the conversion ring 80 is first snapped into the shell component 12 to convert the shell component engagement mechanism from a snap-fit to a taper-fit. Then the second bearing component is pressed into the shell and ring assembly. The conversion ring 80 may be used during a primary hip surgery to allow an intraoperative choice of bearing components 14, 16. The conversion ring 80 may be used during a revision hip surgery to allow a previously implanted bearing component to be replaced by a new bearing component having a different engagement mechanism than the original without having to remove the shell component 12. This is desirable, for example, where the shell component 12 is well fixed in the acetabulum and only the bearing component needs to be changed due to wear or the need for a different bearing configuration such as a different material, shape, or size. The conversion ring 80 also permits the use of independently designed shell and bearing components with one another such as a later designed liner with an earlier designed shell or the use of components from distinct design families.

Although examples of an acetabular cup conversion ring and its use have been described and illustrated in detail, it is to be understood that the same is intended by way of illustration and example only and is not to be taken by way of limitation. The invention has been illustrated in use to convert a snap-fit shell engagement mechanism to a taper-fit shell engagement mechanism. However, the acetabular cup conversion ring may be configured to convert any shell engagement mechanism into any other shell engagement mechanism. Accordingly, variations in and modifications to the acetabular cup conversion ring and its use will be apparent to those of ordinary skill in the art, and the following claims are intended to cover all such modifications and equivalents.

What is claimed is:

1. A kit of acetabular components for assembling an acetabular joint prosthesis including a shell component and a bearing component disposed in the shell, the kit comprising:
   a shell component having an external surface shaped for engagement with an acetabulum and an internal surface defining an internal cavity and a shell engagement mechanism;
   a first bearing component having an external surface dimensioned for receipt within the internal cavity of the shell component, the external surface of the first bearing component defining a first bearing engagement mechanism, the first bearing engagement mechanism engageable with the shell engagement mechanism of the shell component to secure the first bearing component at least partially within the internal cavity of the shell component;
   a conversion ring having a sidewall defining an outer surface and an inner surface and extending axially from a first end to a second end, the outer surface defining a first conversion ring engagement mechanism, the first conversion ring engagement mechanism releasably engageable with the shell engagement mechanism of the shell component, the inner surface of the conversion ring defining a second conversion ring engagement mechanism;
   a second bearing component having an external surface dimensioned for receipt within the internal cavity of the shell component and within the conversion ring, the external surface of the second bearing component defining a second bearing engagement mechanism releasably engageable with the second conversion ring engagement mechanism of the conversion ring, wherein the conversion ring is resiliently collapsible upon insertion into the shell component to engage the first conversion ring engagement mechanism of the conversion ring with the shell engagement mechanism of the shell component.

2. The kit of claim 1 wherein the shell engagement mechanism of the shell component comprises an annular groove, and the first bearing engagement mechanism of the first bearing component and the first conversion ring engagement mechanism of the conversion ring both comprise a relatively resilient portion for snapping into the annular groove of the shell component.

3. The kit of claim 2 wherein the first conversion ring engagement mechanism of the conversion ring comprises a first tapered surface and the second conversion ring engagement mechanism comprises a second tapered surface, whereby the conversion ring is intraoperatively engageable with the shell engagement mechanism of the shell component to convert the shell component from a snap-fit to a taper-fit.

4. The kit of claim 3 wherein the first bearing engagement mechanism of the first bearing component and the first conversion ring engagement mechanism of the conversion ring both comprise an annular projection.

5. The kit of claim 4 wherein the shell engagement mechanism of the shell component further comprises first and second annular grooves formed in the shell component, the grooves being spaced apart axially with the second annular groove being further into the shell component than the first annular groove, the annular projection of the first bearing component engageable with the first annular groove of the shell component and the annular projection of the conversion ring engageable with the second annular groove of the shell component.

6. The kit of claim 3 wherein the second bearing engagement mechanism of the second bearing component and the second conversion ring engagement mechanism of the conversion ring cooperate to form a self locking taper connection.

7. The kit of claim 1 wherein the first bearing component comprises a polymer body and the first bearing engagement mechanism comprises a relatively flexible projection formed on the external surface of the first bearing component, the external surface of the first bearing component engageable with the internal cavity of the shell component, and wherein the second bearing component comprises a relatively rigid non-polymeric body having a relatively rigid external surface, the relatively rigid external surface defining a tapered engagement surface that forms the second bearing engagement mechanism.

8. The kit of claim 1 wherein a portion of the sidewall of the conversion ring is slit to allow the conversion ring to resiliently compress and expand.

9. The kit of claim 8 wherein the sidewall of the conversion ring includes multiple slits extending part-way through the sidewall between the first and second ends with adjacent slits alternately originating from the first and second ends to form the sidewall into a serpentine sidewall.

10. The kit of claim 1 further comprising a plurality of conversion rings and a plurality of second bearing components, each of the plurality of conversion rings having a different second conversion ring engagement mechanism and each of said plurality of second bearing components having a different second bearing engagement mechanism, wherein each of the plurality of conversion rings is configured to adapt the shell component to receive a different one of said plurality of second bearing components.

11. A kit of acetabular components for assembling an acetabular joint prosthesis including a shell component and a bearing component disposed in the shell, the kit comprising:
    a shell component having an external surface shaped for engagement with an acetabulum and an internal surface defining an internal cavity and a shell engagement mechanism;
    a first bearing component having an external surface dimensioned for receipt within the internal cavity of the shell component, the external surface of the first bearing component defining a first bearing engagement mechanism, the first bearing engagement mechanism engageable with the shell engagement mechanism of the shell component to secure the first bearing component at least partially within the internal cavity of the shell component;
    a conversion ring having a sidewall defining an outer surface and an inner surface and extending axially from a first end to a second end, the outer surface defining a first conversion ring engagement mechanism, the first conversion ring engagement mechanism releasably engageable with the shell engagement mechanism of the shell component, the inner surface of the conversion ring defining a second conversion ring engagement mechanism;

a second bearing component having an external surface dimensioned for receipt within the internal cavity of the shell component and within the conversion ring, the external surface of the second bearing component defining a second bearing engagement mechanism releasably engageable with the second conversion ring engagement mechanism of the conversion ring;

wherein the shell engagement mechanism of the shell component comprises an annular groove, and the first bearing engagement mechanism of the first bearing component and the first conversion ring engagement mechanism of the conversion ring both comprise a relatively resilient portion for snapping into the annular groove of the shell component;

wherein the first conversion ring engagement mechanism of the conversion ring comprises a first tapered surface and the second conversion ring engagement mechanism comprises a second tapered surface, whereby the conversion ring is intraoperatively engageable with the shell engagement mechanism of the shell component to convert the shell component from a snap-fit to a taper-fit;

wherein the first bearing engagement mechanism of the first bearing component and the first conversion ring engagement mechanism of the conversion ring both comprise an annular projection; and wherein the shell engagement mechanism of the shell component further comprises first and second annular grooves formed in the shell component, the grooves being spaced apart axially with the second annular groove being further into the shell component than the first annular groove, the annular projection of the first bearing component engageable with the first annular groove of the shell component and the annular projection of the conversion ring engageable with the second annular groove of the shell component.

12. The kit of claim 11 wherein the second bearing engagement mechanism of the second bearing component and the second conversion ring engagement mechanism of the conversion ring cooperate to form a self locking taper connection.

13. The kit of claim 11 wherein the first bearing component comprises a polymer body and the first bearing engagement mechanism comprises a relatively flexible projection formed on the external surface of the first bearing component, the external surface of the first bearing component engageable with the internal cavity of the shell component, and wherein the second bearing component comprises a relatively rigid non-polymeric body having a relatively rigid external surface, the relatively rigid external surface defining a tapered engagement surface that forms the second bearing engagement mechanism.

14. The kit of claim 11 wherein the conversion ring is resiliently collapsible upon insertion into the shell component to engage the first conversion ring engagement mechanism of the conversion ring with the shell engagement mechanism of the shell component.

15. The kit of claim 14 wherein a portion of the sidewall of the conversion ring is slit to allow the conversion ring to resiliently compress and expand.

16. The kit of claim 15 wherein the sidewall of the conversion ring includes multiple slits extending part-way through the sidewall between the first and second ends with adjacent slits alternately originating from the first and second ends to form the sidewall into a serpentine sidewall.

17. The kit of claim 11 further comprising a plurality of conversion rings and a plurality of second bearing components, each of the plurality of conversion rings having a different second conversion ring engagement mechanism and each of said plurality of second bearing components having a different second bearing engagement mechanism, wherein each of the plurality of conversion rings is configured to adapt the shell component to receive a different one of said plurality of second bearing components.

* * * * *